(12) United States Patent
Albertsson et al.

(10) Patent No.: US 9,186,384 B2
(45) Date of Patent: *Nov. 17, 2015

(54) USE OF PLANT CELL MEMBRANE TREATMENT OF OBESITY

(71) Applicant: Thylabisco AB, Lund (SE)

(72) Inventors: Per-Ake Albertsson, Lund (SE); Charlotte Erlansson-Albertsson, Lund (SE)

(73) Assignee: Thylabisco AB, Lund (SE)

( * ) Notice: Subject to any disclaimer, the term of this patent is extended or adjusted under 35 U.S.C. 154(b) by 18 days.

This patent is subject to a terminal disclaimer.

(21) Appl. No.: 14/138,471

(22) Filed: Dec. 23, 2013

(65) Prior Publication Data

US 2014/0220084 A1    Aug. 7, 2014

Related U.S. Application Data

(62) Division of application No. 13/033,871, filed on Feb. 24, 2011, now Pat. No. 8,642,098, which is a division of application No. 11/916,945, filed as application No. PCT/SE2006/000676 on Jun. 9, 2006, now abandoned.

(30) Foreign Application Priority Data

Jun. 10, 2005 (SE) .................................. 0501336-2

(51) Int. Cl.
| | | |
|---|---|---|
| A61K 36/00 | (2006.01) | |
| A61K 36/21 | (2006.01) | |
| A61K 36/28 | (2006.01) | |
| A61K 36/81 | (2006.01) | |
| A61K 36/899 | (2006.01) | |
| A61K 36/02 | (2006.01) | |
| A23L 1/29 | (2006.01) | |
| A23L 1/30 | (2006.01) | |
| A23L 1/305 | (2006.01) | |
| A61K 35/12 | (2015.01) | |
| A61K 35/74 | (2015.01) | |
| A61K 38/10 | (2006.01) | |
| A61K 38/16 | (2006.01) | |
| A61K 36/288 | (2006.01) | |
| A61K 36/31 | (2006.01) | |
| A61K 36/48 | (2006.01) | |
| A61K 38/02 | (2006.01) | |
| A61K 38/05 | (2006.01) | |
| A61K 38/06 | (2006.01) | |
| A61K 38/07 | (2006.01) | |
| A61K 38/08 | (2006.01) | |

(52) U.S. Cl.
CPC ............... *A61K 36/02* (2013.01); *A23L 1/293* (2013.01); *A23L 1/3002* (2013.01); *A23L 1/3053* (2013.01); *A61K 35/12* (2013.01); *A61K 35/74* (2013.01); *A61K 36/00* (2013.01); *A61K 36/21* (2013.01); *A61K 36/28* (2013.01); *A61K 36/288* (2013.01); *A61K 36/31* (2013.01); *A61K 36/48* (2013.01); *A61K 36/81* (2013.01); *A61K 36/899* (2013.01); *A61K 38/02* (2013.01); *A61K 38/05* (2013.01); *A61K 38/06* (2013.01); *A61K 38/07* (2013.01); *A61K 38/08* (2013.01); *A61K 38/10* (2013.01); *A61K 38/16* (2013.01)

(58) Field of Classification Search
CPC ....... A61K 36/00; A61K 36/21; A61K 36/28; A61K 36/81; A61K 36/899; A61K 35/66
USPC .............................. 424/750, 751, 725, 195.17
See application file for complete search history.

(56) References Cited

U.S. PATENT DOCUMENTS

| | | |
|---|---|---|
| 5,593,866 A | 1/1997 | Hancock et al. |
| 2003/0175374 A1 | 9/2003 | Purcell |
| 2005/0048148 A1* | 3/2005 | Anderson et al. ............. 424/774 |

FOREIGN PATENT DOCUMENTS

| | | |
|---|---|---|
| WO | WO 0068386 | 11/2000 |
| WO | WO 03/003835 A1 | 1/2003 |
| WO | WO 2004/016092 | 2/2004 |
| WO | WO 2004/052380 A1 | 6/2004 |
| WO | WO 2005/027944 | 3/2005 |
| WO | WO 2005/027944 A1 | 3/2005 |

OTHER PUBLICATIONS

Alberti et al. "Harmonizing the Metabolic Syndrome: A Joint Interim Statement of the International Diabetes Federation Task Force on Epidemiology and Prevention; National Heart, Lung, and Blood Institute; American Heart Association: World Heart Federation: International Atherosclerosis Society; and International Association for the Study of Obesity." *Circulation. AHA*. vol. 120. 2009. pp. 1640-1645.

Friso et al. "In-Depth Analysis of the Thylakoid Membrane Proteome of *Arabidopsis thaliana* Chloroplasts: New Proteins, New Functions, and a Plastid Proteome Database." *The Plant Cell*. vol. 16. 2004. pp. 478-499.

Albertsson et al. "Separation of Membrane Components by Partition in Detergent-Containing Polymer Phase Systems: Isolation of the Light Harvesting Chlorophyll a/b Protein." *J. of Chromatography*. vol. 215. 1981. pp. 131-141.

(Continued)

*Primary Examiner* — Chris R Tate
*Assistant Examiner* — Deborah Davis
(74) *Attorney, Agent, or Firm* — Merchant & Gould P.C.

(57) ABSTRACT

The present invention relates to the use of a composition comprising at least one cell membrane fraction or parts thereof, for the reduction of lipolytic activity and/or to retard fat digestion, suppress appetite, body weight and/or lower blood lipids. The invention also relates to the use of said hydrophobic peptide in a pharmaceutical as well as a food composition and methods of treating a mammal with said composition.

19 Claims, 4 Drawing Sheets

(56) References Cited

OTHER PUBLICATIONS

Albertsson. "Partition of Cell Particles and Macromolecules: Separation and Purification of Biomolecules, Cell Organelles, Membranes, and Cells in Aqueous Polymer Two-Phase Systems and their use in Biochemical Analysis and Biotechnology." *A Wiley-Interscience Publication*. 1986. pp. 153-156.

Althage et al. "Cross-linking of transmembrane helices in proton-translocating nicotinamide nucleotide transhydrogenase from *Escherichia coli*: implications for the structure and function of the membrane domain." *Biochimica et Biophysica Acta*. vol. 1659. 2004. pp. 73-82.

Borgstrom et al. "Pancreatic Lipase and Co-Lipase: Interactions and Effects of Bile Salts and Other Detergents." *Eur. J. Biochem*. vol. 37. 1973. pp. 60-68.

Bradford. "A Rapid and Sensitive Method for the Quantitation of Microgram Quantities of Protein Utilizing the Principle of Protein-Dye Binding." *Analytical Biochemistry*. vol. 72. 1976. pp. 248-254.

Chloroplast. Retreived from the internet. http://en.wikipedia.org/wiki/Chlorplast. Retrieved on Nov. 19, 2010. p. 1-5.

Danielsson et al. "Quantification of photosystem I and II in different parts of the thylakoid membrane from spinach." *Biochimica et Biophysica Acta*. vol. 1608. 2004. pp. 53-61.

Danielsson et al. "Quantification of photosystem I and II in different plants of the thylakoid membrane from spinach." *Biochimica et Biophysica Acts*. vol. 1608. 2004. pp. 53-61.

Greenberg et al. "The Controls of Fat Intake." *Psychosomatic Medicine*. vol. 58. 1996. pp. 559-569.

Hill et al. "Oral Administration of Proteinase Inhibitor II from Potatoes Reduces Energy Intake in Man." *Physiology & Behavior*. vol. 46. 1990. pp. 241-246.

Kjellboom et al. "Preparation and polypeptide composition of chlorophyll-free plasma membranes from leaves of light-grown spinach and barley." *Physiol. Plant*. vol. 62. 1984. pp. 501-509.

Kuttkat et al. "Light-Harvesting Chlorphyll a/b-Binding Protein Inserted into Isolated Thylakoids Binds Pigments and is Assembled into Trimeric Light-Harvesting Complex." *Plant Physiol*. vol. 109. 1995. pp. 1267-1276.

Lindqvist et al. "Overeating of palatable food is associated with blunted leptin and ghrelin responses." *Regulatory Peptides*. vol. 130. 2005. pp. 123-132.

Mason. "Nucleotide Sequence of a cDNA encoding the light-harvesting chlorophyll a/b binding protein from spinach." *Nucleic Acids Research*. vol. 17. No. 13. 1989. pp. 5387.

Nakai et al. "Inhibitory Effects of Oolong Tea Polyphenols on Pancreatic Lipase in Vitro." *Journal of Agricultural & Food Chemistry*. vol. 53. 2005. pp. 4593-4598.

Norling et al. "2D-isoloation of pure plasma and thylakoid membranes from the cyanobacterium *Synechocystis* sp. PCC 6803."*FEBS Letters*. vol. 436. 1998. pp. 189-192.

Petit et al. "Some properties of mitochondria, mitoplasts and submitochondrial particles of different polarities from plant tissues." *Biochimica et Ciophysica Acta*. vol. 890. 1987. pp. 377-386.

Phototroph.blogspot.com Retrieved from the internet on Jul. 29, 2012 http://phototroph.blogspot.com/2006/12/chloroplast.html.—3 pages.

Romanowska et al. "Isolation and Characterization of the Cytochrome *bf* Complex from Whole Thylakoids, Grana, and Stroma Lamellae Vesicles from Spinach Chloroplasts." *Plant Cell Physiol*. vol. 35. No. 4. 1994. pp. 557-568.

Sjostrom et al. "Randomised placebo-controlled trial of orlistat for weight loss and prevention of weight regain in obese patients." *The Lancet*. vol. 352. 1998. pp. 167-172.

Spinach. Retrieved from the internet. Web archive date Feb. 28, 2004. http://web.archive.org/web/20040228174647/http://en.wikipedia.org./wiki/Spinach>. Retrieved on Nov. 19, 2010. 1 page.

Wang et al. "Reversible membrane association of dinitrogenase reductase activating glycohydrolase in the regulation of nitrogenase activity in *Rhodospirillum rubrum*; dependence of FInJ and AmtB1." *FEMS Microbiology Letters*. vol. 142. 2005. pp. 273-279.

Yang et al. "Antihypertensive Properties of Spinach Leaf Protein Digests." *J. Agric. Food Chem*. vol. 52. 2004. pp. 2223-2225.

Yang et al. "Isolation and Antihypertensive Effect of Angiotensin I-Converting Enzyme (ACE) Inhibitory Peptides from Spinach Rubisco." *J. Agric. Food Chem*. vol. 51. 2003. pp. 4897-4902.

"Super-concentrated nutritive composition for reducing weight", DERWENT, May 29, 1996, XP002190285.

"Preparing process for haw and ginkgo leaf capsule", Derwent, Mar. 13, 2002, XP002315397.

\* cited by examiner

1

USE OF PLANT CELL MEMBRANE TREATMENT OF OBESITY

This application is a Divisional of U.S. Ser. No. 13/033,871, filed 24 Feb. 2011, which is a Divisional of U.S. Ser. No. 11/916,945, filed 24 Apr. 2009, which is a National Stage Application of PCT/SE2006/000676, filed 9 Jun. 2006, which claims benefit of Serial No. 0501336-2, filed 10 Jun. 2005 in Sweden and which applications are incorporated herein by reference. To the extent appropriate, a claim of priority is made to each of the above disclosed applications.

FIELD OF INVENTION

The present invention relates to the use of a composition comprising at least one cell membrane or parts thereof, for the reduction of lipolytic activity and/or to retard fat digestion, suppress appetite, body weight and/or lower blood lipids. The invention also relates to the use of said hydrophobic peptide in a pharmaceutical as well as a food composition and methods of treating a mammal with said composition.

BACKGROUND OF INVENTION

Overweight and obesity has become an increasing worldwide problem. Obesity leads to a concomitant increase in several diseases such as diabetes, arteriosclerosis, hypertension as well as certain cancer forms. High-fat diet, either alone or added with sucrose, is one of the most important factors causing obesity, since these diets easily promote overeating. It is therefore of great importance to optimize the control of appetite for dietary fat to reduce obesity. Satiety for fat is mainly driven from the intestine, as demonstrated through the infusion of fat into the intestine, which reduces food intake (Greenberg D. and Smith, G. P., Psychosomatic medicine 58: 559-569, 1996). The reason for the suppression of food intake under these conditions is the release of various satiety peptides in the intestine by the contact of fat with the intestinal mucosa. Since fatty acids, the products of dietary fat, are absorbed immediately after their production, a reduced rate of fat digestion would theoretically optimize the satiety for fat.

The key enzyme during intestinal fat digestion is pancreatic lipase. The use of lipase inhibitor (Xenical) as a drug against obesity is well established (Sjöstrom L. et al, Lancet 352: 167-172, 1998). The lipase inhibitor not only reduces body weight but also improves insulin resistance. Such findings hence provide strong evidence for a role of intestinal fat digestion on satiety for fat and insulin sensitivity. The drawback with this lipase inhibitor is that it inhibits all types of lipases and produces steatorrea due to a strongly impaired fat digestion. It is therefore of utmost importance to develop a natural compound that retards fat digestion in a milder way without causing steatorrea as side effect. We have found a natural compound of high nutritive value that retards fat digestion, suppresses appetite by increasing satiety hormones and decreases serum triglyceride levels.

SUMMARY OF THE INVENTION

The present invention relates to the use of a composition, for the reduction of lipolytic activity and/or to retard fat digestion, suppress appetite, body weight and/or lower blood lipids. By reducing the lipolytic activity fat digestion will be retarded and the appetite suppressed and thereby an enhanced satiety for prevention of for example obesity.

In a first aspect the invention relates to the use of a composition comprising at least one cell membrane or parts thereof, for the reduction of lipolytic activity and/or to retard fat digestion, suppress appetite, body weight and/or lower blood lipids.

According to a second aspect the invention relates to the use of said composition as a pharmaceutical composition.

According to a third aspect the invention relates to the use of said composition as a food composition.

The invented composition may be used to regulate the appetite, such as for the treatment of the metabolic syndrome either as a disease or a disorder.

Figure 1:
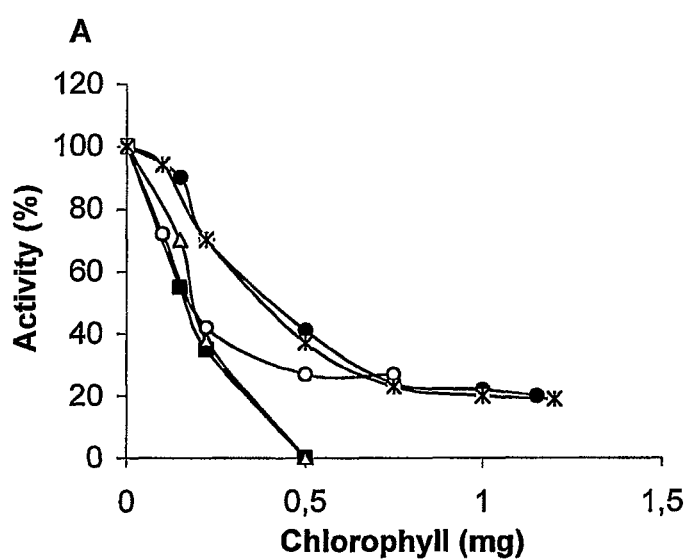
FIG. 1 shows the inhibition of pancreatic lipase by biological membranes from leaves. Chloroplast membranes from spinach (filled circles); clover (black squares); *Arabidopsis thaliana* (triangles); rape (circles) and sugar beet (crosses).

Data on body weight gain, serum triglycerides and plasma cholecystokinin after onset of thylakoid treatment are shown in Table 1.

DETAILED DESCRIPTION OF THE INVENTION

Definitions

In the context of the present application and invention, the following definitions apply:

The term "cell membrane" is intended to mean a modified or unmodified natural or synthetically made biological cell membrane, of animal, plant, or microbial origin, wherein the cell membrane comprises intact cell membranes or fractions thereof as well as parts thereof or mixtures of parts and intact cell membranes, such as the hydrophobic peptides or hydrophobic proteins of said cell membrane. Part of the cell membrane may be between 0.1 to 0.5 µm and may solely comprise one or more membrane spanning peptides.

The term "hydrophobic peptide" is intended to mean a peptide having at least 85% hydrophobic amino acid residues selected from the group consisting of alanine, valine, leucine, isoleucine, proline, phenylanaline, tryptophane, methionine, glycine, cysteine together with a few amino acids with charged residues such as arginine and glutamic acid.

The term "lipolytic activity" is intended to mean the rate of hydrolysis of lipids by lipases.

The term "membrane spanning peptide" is intended to mean at least the amino acid residues, which form the membrane spanning part of the protein. The peptide may be one or more membrane spanning parts of one membrane spanning proteins, such as a stretch comprising between 15 to 25 amino acid residues and multiples thereof.

Composition

The invention relates to the use of a composition comprising at least one cell membrane or parts thereof, for the reduction of lipolytic activity and/or to retard fat digestion, suppress appetite, body weight and/or lower blood lipids. By reducing the lipolytic activity it is possible to retard fat digestion, suppress appetite, body weight and/or lower blood lipids. Thereby it is possible for the first time to efficiently regulate the appetite of a mammal, such as a human being or another animal. By enabling the possibility to regulate the lipolytic activity a slow formation of fatty acids in the intestine will promote and prolong satiety.

The composition may comprise at least the membrane spanning part of a biological protein, wherein said membrane spanning part comprises hydrophobic amino acid residues. Accordingly the composition comprises a biological membrane or parts thereof, wherein said biological membrane comprises at least said hydrophobic peptide. The composition may comprises at least one cell membrane hydrophobic peptide having from about 15 to about 25 amino acid residues, such as 2, 3, 4 or 5 hydrophobic peptides being derived from one and the same protein or different proteins and the composition may comprise Biological cell membranes for example occur in all living cells and constitute a large part of the cell mass. Examples of cell membrane fractions according to the invention are cell membrane fractions obtained from animals, plants, algaes, microorganisms or cell membrane fractions of parts thereof, which are synthetic or a mixture thereof. In prokaryotes, there are single or double plasma membranes and in photosynthesising bacteria also the photosynthetic membrane, the thylakoids. In eukaryotes the membranes include the plasma membrane, the endoplasmic reticulum, the Golgi membrane, the nuclear membrane, the lysosomal membrane, the mitochondrial membranes and for the green algae and plants also the chloroplast membranes which include the two envelope membranes and the photosynthetic membrane, the thylakoids. Biological membranes are composed of proteins and lipids. All biological membranes contain intrinsic membrane proteins with one or several membrane spanning polypeptide chains composed of hydrophobic amino acids. Most of the lipids, such as phospholipids and galactolipids, form bilayers in which the intrinsic membrane/membrane spanning proteins are embedded. In addition, extrinsic proteins are attached to the surface of the membrane. The thylakoids are responsible for photosynthesis in plants, green algae, and in the photosynthetic bacteria such as blue-green and purple bacteria. The thylakoid membrane consists of proteins and lipids in about 70/30 per cent ratio. There are more than 100 different proteins in the membrane; the lipid fraction is dominated by galactolipids with the main fatty acids being of the omega-3 type. In addition the thylakoid membrane contains several different pigments, chlorophyll a, chlorophyll b, plastoquinones, the carotenoids β-carotene, luteine, violaxanthin and neoxanthin. This means that the thylakoids have a composition of high nutrition value and the same applies to synthetic membranes having the same or substantially the same composition as the thylakoids, i.e., chloroplasts as well as the thylakoids may be used in the food additive as well as in the food product of the invention. Examples of biological membranes are the chloroplasts or the thylakoid membranes and the membranes may be obtained from clover, rape, sugar beet, dandelion, *Arabidopsis thaliana*, maize, tobacco, sun flower, salad, *Chenopodium, Atriplex*, spinach and grasses or a mixture thereof.

Accordingly, if the composition comprises at least one hydrophobic peptide, said peptide may have a length of 16, 17, 18, 19, 20, 21, 22, 23 or 24 amino acid residues. Examples of peptides are shown in SEQ ID NO:1, SEQ ID NO:2 or SEQ ID NO:3 or mixtures thereof as well as the peptides may be operably linked to each other. The amino acid residues may be selected from the group consisting of alanine, valine, leucine, isoleucine, proline, phenylanaline, tryptophane, methionine, glycine, cysteine together with a few amino acids with charged residues such as arginine and glutamic acid. The amino acid residues and the peptide may be synthetic or naturally occurring and the same applies for the amino acid residues, i.e., they may be natural or synthetic ones as long as they are hydrophobic or carries a charged residue. The membrane fraction may be a cell membrane fraction, which has been treated with one or more enzymes to provide smaller pieces of the cell membranes.

Said biological membrane or part thereof of the invention may have a size distribution of 0.1 μm to about 5 μm, such as 0.1, 0.2, 0.3, 0.4, 0.5 or 1.0 μm.

Additionally the hydrophobic peptide may have from about 1 to about 50 additional amino acid residues and may also be modified by amidation, esterification, acylation, acetylation, PEGylation or alkylation.

The photosynthetic membranes are the most abundant, with respect to mass, of all biological membranes on earth. Green leaves from plants constitute a convenient and abundant source for isolation and preparation in large quantity of chloroplast membranes for the purpose of this invention.

Biological membranes can be isolated in many different ways, such as those mentioned in the examples. The most common being to first disintegrate the cells mechanically which yields membrane vesicles with different size and composition. Large cell debris are removed by low speed centrifugation and the membrane vesicles of the supernatant, then, collected by differential centrifugation or gradient centrifugation. Alternatively the large cell debris is removed by filtration, and the membrane vesicles collected by centrifugation.

It is also possible to design methods, which do not involve centrifugation. In this case the large cell debris is first removed by filtration. The cell membranes can then be flocculated i.e. precipitated by different procedures such as:

1 Addition of acid or a base such that a pH is reached when precipitation is achieved, 2. Additions of polymers with more or less different charged groups, which induce precipitation, 3. Heating the vesicle suspension such as between 40-100 degree Celsius.

4. Collection of vesicles by partitioning in an aqueous two phase system whereby the vesicles are concentrated into a small volume phase (Albertsson P. Å. Partition of cell Particles and macromolecules. Wiley, New York, 1986)

5. Collection at an interface of a liquid-liquid two-phase system, such as the phase system given in 4) or a water-oil phase system.

6. Collection at an interface of a water-oil phase system leading to an emulsion.

7. Adsorption onto solid material such as calcium phosphate, silica, various ion exchange resins.

8. Freezing and thawing whereby the water crystals formed concentrate the vesicles into aggregates, which after thawing flocculate.

The hydrophobic peptides may be synthesised by standard chemical methods, including synthesis by automated procedure. In general, peptide analogues are synthesised based on the standard solid-phase Fmoc protection strategy with HATU (N-[DIMETHYLAMINO-1H-1.2.3.-TRIAZOLO[4,5-B]PYRIDIN-1-YLMETHYLELE]-N-METHYL-METHANAMINIUM HEXAFLUOROPHOSPHATE N-OXIDE) as the coupling agent or other coupling agents such as HOAt-1-HYDROXY-7-AZABENZOTRIAZOLE. The peptide is cleaved from the solid-phase resin with trifluoroacetic acid containing appropriate scavengers, which also deprotects side chain functional groups. Crude peptide is further purified using preparative reversed-phase chromatography. Other purification methods, such as partition chromatography, gel filtration, gel electrophoresis, or ion-exchange chromatography may be used. Other synthesis techniques, known in the art, such as the tBoc protection strategy, or use of different coupling reagents or the like can be employed to produce equivalent peptides.

Peptides may alternatively be synthesised by recombinant production (see e.g., U.S. Pat. No. 5,593,866). A variety of host systems are suitable for production of the peptide analogues, including bacteria, such as *E. coli*, yeast, such as *Saccharomyces cerevisiae* or *pichia*, insects, such as Sf9, and mammalian cells, such as CHO or COS-7. There are many expression vectors available to be used for each of the hosts and the invention is not limited to any of them as long as the vector and host is able to produce the antimicrobial peptide. Vectors and procedures for cloning and expression in *E. coli* can be found in for example Sambrook et al. (Molecular Cloning: A Laboratory Manual, Cold Spring Harbor Laboratory Press, Cold Spring Harbor, N.Y., 1987) and Ausubel et al. (Current Protocols in Molecular Biology, Greene Publishing Co., 1995).

The invented composition may be in any form, such as a natural extract obtained by a conventional method such as one of those mentioned below, as well as being dried, freezed or freeze dried.

The invented composition may be used as a food additive and may be admixed with other components such as fat, butter, margarine, oils, cream, milk, cheese, brie, flour, juices, soft drinks, teas either prior to being added to a food product or during the addition to the food product.

Said food additive or food composition comprising said composition may be solid, semisolid or in a liquid form. Further it may be freeze dried, spray dried or lyophilised. The invented food additive may be used in any kind of food product as well as being used alone. Examples of food products are fat, butter, margarine, oils, cream, milk, cheese, brie, flour, juices, soft drinks, teas. Other examples are yoghurt, ice cream, cakes, bread and dressing.

The invented composition may also be used as a pharmaceutical composition. The pharmaceutical composition comprises the invented composition as well as a pharmaceutically acceptable buffer, excipient, carrier or diluent. Examples of diseases to be treated are the metabolic syndrome either as a disease or a disorder such as hypertension, arteriosclerosis, gout, diabetes type one and two, cancers and dyslipidemia.

"Pharmaceutically acceptable" means a non-toxic material that does not decrease the effectiveness of the biological activity of the active ingredients, i.e., the antimicrobial peptide(s). Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition.

The excipient may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The compositions of the invention may also be in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the peptide.

The pharmaceutical compositions may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

Suitable preparation forms are, for example granules, powders, tablets, coated tablets, (micro) capsules, syrups, emulsions, microemulsions, defined as optically isotropic thermodynamically stable systems consisting of water, oil and surfactant, liquid crystalline phases, defined as systems characterised by long-range order but short-range disorder (examples include lamellar, hexagonal and cubic phases, either water- or oil continuous), or their dispersed counterparts, gels, ointments, dispersions, suspensions, creams, aerosols, droplets or injectable solution in ampoule form and also preparations with protracted release of active compounds, in whose preparation excipients, diluents, adjuvants or carriers are customarily used as described above.

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the, activity of the compound, manner of administration, nature and severity of the disorder, age and body weight of the patient different doses may be needed. The administration of the dose can be carried out both by single administration in the form of an individual dose unit or else several smaller dose units and also by multiple administration of subdivided doses at specific intervals.

The present invention concerns both humans and other mammal such as horses, dogs, cats, cows, pigs, camels, among others. Thus the methods are applicable to both human therapy and veterinary applications. The objects, suitable for such a treatment may be identified by well-established hallmarks.

Here follows, as an example of the invention, a description of the isolation of chloroplast membranes, the thylakoids, from spinach and their application in inhibition of the pancreatic lipase activity and reduction of food intake. Following examples are intended to illustrate, but not to limit, the invention in any manner, shape, or form, either explicitly or implicitly.

Example 1

Preparation of Membranes and Membrane Proteins

Thylakoids were isolated as described in Danielsson et al. Biochim Biophys Acta 1608, 53-61 (2004) for use in the lipase assay. For preparing food, the thylakoids were isolated as follows: Leaves were homogenised in a blender and filtered through four layers of nylon mesh (20 µm). The filtrate was centrifuged at 5000 g for 10 min to collect the thylakoids. These were washed by resuspension in water and recentrifuged as before. Lipid extraction: 4 ml thylakoid suspension (3.8 mg chlorophyll/mL) mixed with 40 mL chloroform/methanol was incubated for 1 hr on ice. After centrifugation at 4000 g for 10 min the pellet was extracted for a second time and centrifuged as before. The pellet was dried in air and extracted with 10 mL of the buffer solution used for thylakoid isolation on ice to remove water soluble proteins. The mixture was centrifuged at 4000 g for 10 min and the pellet collected. This is named "membrane protein fraction" (FIG. 1). Trypsin treatment was carried out by incubating the thylakoids with 300 µg trypsin (Sigma type III)/mg chlorophyll, in 20 mM phosphate buffer (pH 7.4), for 45 min at 37° C. After adding 1 mM phenylmethylsulphonyl fluoride (PMSF), to inhibit the trypsin, the thylakoids were collected by centrifugation for 10 min at 900 g. Chlorophyll was determined as described above (Danielsson et al. Biochem Biophys Acta 1608, 53-61 (2004) and protein according to Bradford (Bradford, M. M. Anal Biochem 72, 248-54 (1976)). Light harvesting complex II (LHCII) was prepared as described in Andersson, B. & Albertsson, P.-Å. J. Chromatogr. 890, 131-141 (1981). Mitochondria prepared from potato tubers according to (Petit, P. X., Edman, P., Gardestrom, P. & Ericson, I. Biochim Biophys Acta 890, 377-386 (1987)). Plasma membranes from spinach leaves prepared according to (Kjellbom, P. & Larsson, C. Physiol Plant 62, 501-509 (1984)). Membranes from *Synechosystis* prepared according to (Norling, B., Zak, E., Andersson, B. & Pakrasi, H. FEBS Lett 436, 189-92 (1998))Chromatophores from *Rhodospirillum rubrum* prepared according to (Wang, H., Franke, C. C., Nordlund, S. & Noren, A. FEMS Microbiol Lett 253: 273-279 (2005)). Before use, extrinsic water soluble proteins were removed by washing with 0.5 M NaCl, 25 mM Tris-HCl, pH 7.8 followed by two washings with the Tris buffer only according to (Wang, H., Franke, C. C., Nordlund, S. & Noren, A. FEMS Microbiol Lett 253: 273-279 (2005)). Transhydrogenase prepared according to (Althage, M. et al. Biochim Biophys Acta 1659, 73-82 (2004)) from *E. coli*. Cytochrome $b_6f$ from spinach leaves were prepared according to (Romanowska, E. & Albertsson, P.-Å. Plant Cell Physiol 35, 557-568 (1994)).

Example 2

Crude Preparation of Cell Membranes (Thylakoids)

Leaves of spinach, either fresh or frozen, were cut into pieces. These were suspended in water and disintegrated by a mechanical mincer until most of the cells are broken. The slurry was then filtered through a nylon net with a pore size of 20 µm. The filtrate is centrifuged at 2000×g for 5 min. The pellet was resuspended in water and recentrifugated at 2000×g for 5 min. The pellet was stored frozen or dried. Alternatively, a precipitating agent was added to the filtrate: The filtrate was acidified by addition of acid to a low pH, such as pH 4-5, so that the membranes precipitate. The precipitate was washed by resuspension in water at pH 4-5 and resettling of the precipitate. The precipitate is collected.

Example 3

Preparation of Crude Cell Membrane Fractions

Cells, suspended in water, were further disintegrated mechanically by a mincer until most of the cells are broken. The slurry was filtrated to remove unbroken cells and large fragments of cell walls. The filtrate was centrifuged at 10 000×g for 10 min. The pellet was resuspended and recentrifuged at 10 000×g for 10 min. The pellet was collected and stored frozen or dried.

Example 4

Preparation of Thylakoids from Spinach Using Filtration Only

Leaves of spinach, either fresh or frozen, were cut into pieces. These were suspended in water and disintegrated by a mechanical mincer until most of the cells are broken. The slurry was then filtered through a nylon net with a pore size of 20 µm. To the filtrate is added acetic acid until the pH reaches 4.7 to induce flocculation. When the flocculate has settled in the bottom of the vessel the supernatant is removed by decanting. The flocculate is then put on a filter with a pore size of 20 µm. The flocculated thylakoids stay at the filter and can be washed with water at pH 4.7. The washed thylakoids are collected and after adjusting to a desired pH they are stored frozen or dried.

Example 5

Measurement of the Lipase Activity

The lipase activity was measured according to the following (Borgström B. and Erlanson C. European J. of Biochemistry 37: 60-68, 1973): 15 ml of an aqueous solution containing 1 mM Tris buffer pH 7.0, 1 mM calcium chloride, 150 mM sodium chloride, 4 mM sodiumtaurodeoxycholate, 0.5 μg lipase, 1 μg of colipase.

To this mixture 0.5 ml of tributyrin is added together with increasing amounts of membranes and the released fatty acids measured using a pH stat.

Figure 2:
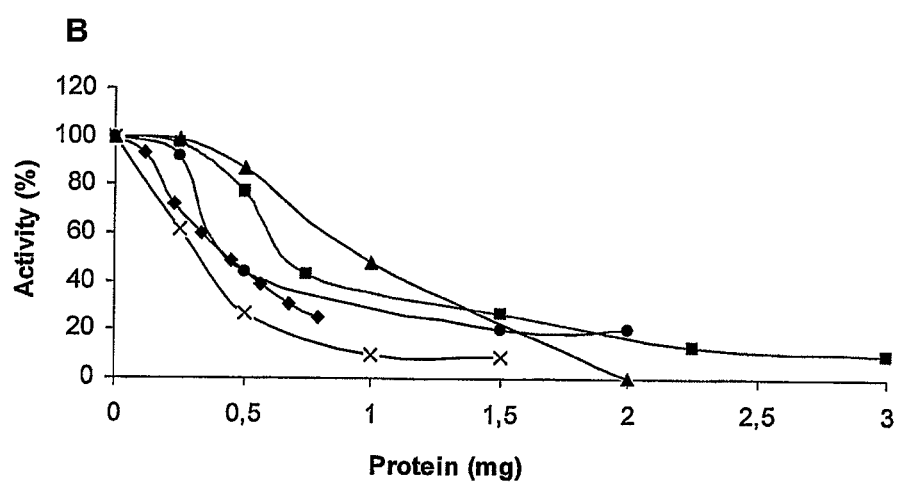
FIG. 2 shows the inhibition of pancreatic lipase by biological membranes: Mitochondria from potato tuber (squares), mitochondria from chicken heart (filled circles), plasma membrane from spinach leaf (diamonds), membranes from *Synechocystis* (crosses) and chromatophores of *Rhodospirillum rubrum* (triangles).
Figure 3:
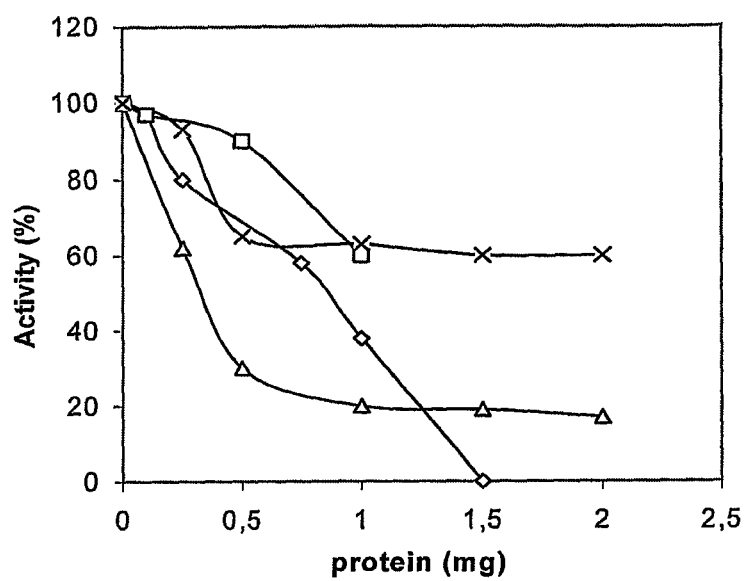
FIG. 3 shows the inhibition of pancreatic lipase by isolated membrane proteins. Light harvesting chlorophyll a/b complex, LHC II (triangles), synthetic polypeptide with the same amino acid sequence (i.e. VIHCRWAMLGALGCVFPELL) as one of the alpha helices of LHCII (crosses), transhydrogenase (diamonds) and cytochrome $b_6f$ complex (squares).

The effect of the biological membranes on lipase activity is shown in FIG. 1-2. The effect of membrane proteins and synthesized polypeptide is further shown in FIG. 3.

Example 6

Production of a Food Product and the Effect on Food Intake

Cakes (500 g, 42% fat by energy) were prepared in the following way:

| Ingredient | Quantity |
| --- | --- |
| Gelatine | 20 g (dissolved in 200 ml water and heated in water-bath to 60-70° C.) |
| Casein | 110 g |
| Starch | 190 g |
| Corn-oil | 15 g |
| Lard | 90 g |
| Mix of vitamin | 5 g |
| Salt mix | 20 g |
| Choline | 1 g |
| Methionine | 1.5 g |
| Cellulose | 47.5 g |

Chloroplast membranes (Thylakoids, containing 1000 mg chlorophyll) suspended in 30 g water Procedure:

Starch and oil was mixed in a food processor (Bosch Universal). The remaining solid ingredients were added, followed by the gelatine solution. After thoroughly mixing, water, with or without chloroplast membranes (thylakoids), was finally added. The cakes were baked in an oven at 70° C. for two days.

The experiment shown in FIG. 4 was performed in the following way.

Female Sprague-Dawley rats (200 g) from B&K, Sollentuna, Sweden were housed in a temperature-controlled room (22±1° C.) under a 12-h light (6:00-18:00)/12-h cycle, given free access to water, and fed ad libitum on a standard chow unless otherwise stated during high-fat diet experiments. All procedures using animals were approved by the Local Animal Ethics Committee Lund, Lund, Sweden.

Feeding Protocol

For measurement of food consumption rats were individually housed in cage and given a high-fat diet for one week before the start of the study. The high-fat diet consisted of a diet, containing by energy 42.1% fat, 23.9% protein and 34.0% carbohydrate with a caloric density of 4.7 kcal/g as described (Lindquist et al. Regul. Pept. 130: 123-132 (2005). The high-fat diet containing thylakoids were prepared as for the high-fat diet with the addition of purified thylakoids at a concentration of 2 mg chlorophyll per gram of food. Food intake was measured daily and body weight at the start and end of the feeding period. Cages were carefully monitored for evidence of food spillage.

TABLE 1

Figure 4:
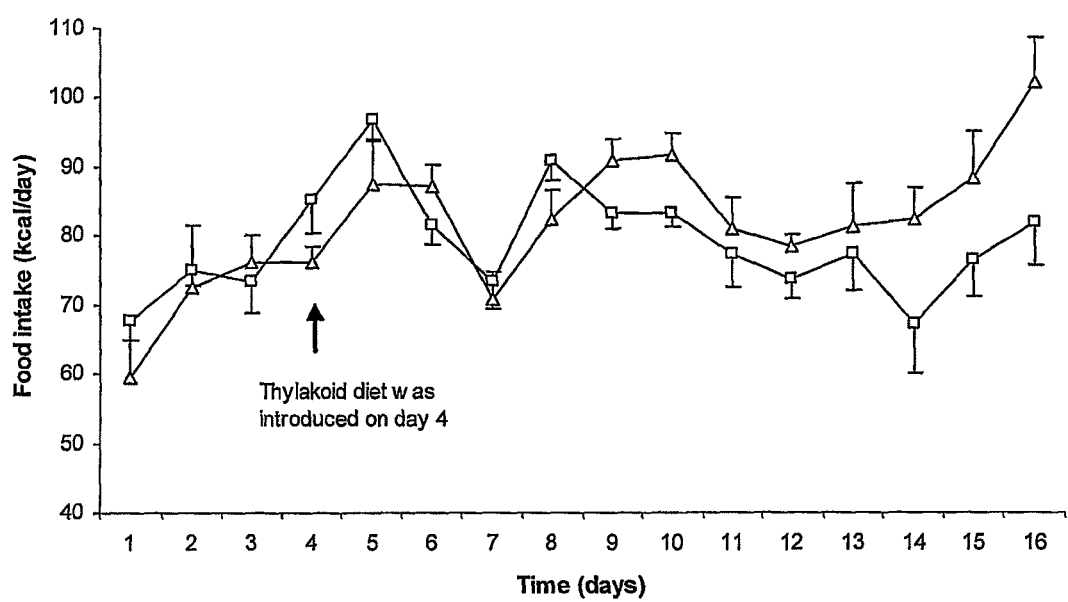
FIG. 4 shows the effect of treatment with chloroplast membranes, (thylakoids) during high-fat diet for eleven days in Sprague-Dawley rat. Food intake with chloroplast membranes (squares) and without (triangles). The daily food intake is given as means±SEM from eight animals in each group (n=8).

Effect of treatment with thylakoids during high-fat diet for eleven days in Sprague-Dawley rat, see FIG. 4.

|  | Control | Thylakoids |
| --- | --- | --- |
| Body weight gain (g) | 60.5 ± 3.55 | 49.9 ± 8.62* |
| Serum TG (mmol/L) | 1.02 ± 0.13 | 0.62 ± 0.04* |
| Plasma CCK (pmol/L) | 0.68 ± 0.08 | 0.86 ± 0.12* |

Values are means ± SE with
*Significance level of P < 0.05 and
**significance level of P < 0.01 between control diet and thylakoid treatment.
TG = triglycerides, CCK = cholecystokinin

Example 7

Food Emulsion

The vegetables (300 g) were allowed to thaw at room temperature for 0.5 hours before they were thoroughly processes in a household mixer. Vegetable juice was obtained by feeding the finely cut pieces of vegetable into a household juice centrifuge.

A smooth well-tasting emulsion was obtained by homogenizing the vegetable juice (60 g) and triglyceride oil (30 g) with a handhelds mixer equipped with stainless steal cutting blades. Emulsions made from broccoli and spinach juice were visually inspected for free oil and/or water phase after 0.5 hours (storage at room temperature) and 10 hours (storage in refrigerator).

| Vegetable | Appearance after 0.5 hour of storage. | Appearance after 10 hour of storage. |
| --- | --- | --- |
| Spinach | No free oil phase, no free water phase | No free oil phase, no free water phase |
| Broccoli | No free oil phase, no free water phase | No free oil phase, free water phase |

The results from the inspection are summarised in table above and show that the oil droplets in the emulsions are very stable since no coalesces could be notice (no free oil phase).

The invention claimed is:

1. A method of reducing body weight in a mammal comprising
administering to a mammal in need thereof an effective amount of a composition comprising an isolated thylakoid membrane or a portion thereof to reduce body weight.

2. The method according to claim 1, wherein the thylakoid membrane or portion thereof, is obtained from a plant, algae or microorganism, or is a mixture thereof.

3. The method according to claim 2, wherein the thylakoid membrane or portion thereof is obtained from clover, rape, sugar beet, dandelion, *Arabidopsis thaliana*, maize, tobacco, sunflower, *Chenopodium*, *Atriplex*, spinach, grasses, or a mixture thereof.

4. The method according to claim 3, wherein the thylakoid membrane or portion thereof is obtained from spinach.

5. The method according to claim 1, wherein the thylakoid membrane or portion thereof comprises hydrophobic amino acid residues.

6. The method according to claim 1, wherein said composition further comprises at least one hydrophobic peptide having from about 15 to about 25 amino acid residues.

7. The method according to claim 1, wherein the composition further comprises two or more hydrophobic peptides being derived from the same protein or different proteins.

8. The method according to claim 1, wherein said composition further comprises hydrophobic peptides comprising 16, 17, 18, 19, 20, 21, 22, 23 or 24 amino acid residues.

9. The method according to claim 1, wherein said composition further comprises hydrophobic peptides comprising SEQ ID NO:1, SEQ ID NO:2, SEQ ID NO:3, or a mixture thereof.

10. The method according to claim 1, wherein the thylakoid membrane or portion thereof has a size distribution of 0.1 μm to about 5 μm.

11. The method according to claim 1, wherein said composition further comprises hydrophobic peptides comprising from about 1 to about 50 additional amino acid residues.

12. The method according to claim 1, wherein said composition further comprises hydrophobic peptides that have been modified by amidation, esterification, acylation, acetylation, PEGylation or alkylation.

13. The method according to claim 1, wherein said composition further comprises a pharmaceutically acceptable carrier, diluent, excipient or buffer.

14. The method according to claim 1, wherein said composition is a food composition.

15. The method according to claim 14, wherein said food composition is margarine, oil, cream, milk, cheese, brie, flour, juice, soft drink or tea product.

16. The method according to claim 1, wherein said composition is freeze dried, spray dried or lyophilised.

17. The method of claim 1, wherein the composition regulates the appetite of the mammal being treated.

18. The method according to claim 1, wherein said composition further comprises hydrophobic peptides comprising SEQ ID NO:1, SEQ ID NO:2, SEQ ID NO:3, or a mixture thereof.

19. The method according to claim 1, wherein the composition reduces lipolytic activity, retards fat digestion, regulates appetite, or lowers blood lipids in the mammal being treated.

* * * * *

SEQUENCE LISTING

<160> NUMBER OF SEQ ID NOS: 3

<210> SEQ ID NO 1
<211> LENGTH: 20
<212> TYPE: PRT
<213> ORGANISM: Artificial Sequence
<220> FEATURE:

-continued

```
<223> OTHER INFORMATION: Synthetic peptide used as an example

<400> SEQUENCE: 1

Val Ile His Cys Arg Trp Ala Met Leu Gly Ala Leu Gly Cys Val Phe
1               5                   10                  15

Pro Glu Leu Leu
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide used as an example

<400> SEQUENCE: 2

Leu Val His Ala Gln Ser Ile Leu Ala Ile Trp Ala Cys Gln Val Ile
1               5                   10                  15

Leu Met Gly Ala Val
            20

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide used as an example

<400> SEQUENCE: 3

Leu Ala Met Phe Ser Met Phe Gly Phe Phe Val Gln Ala Ile Val Thr
1               5                   10                  15

Gly
```